United States Patent [19]

Bechara et al.

[11] 4,232,152

[45] Nov. 4, 1980

[54] AMINE SALTS OF TERTIARY AMINO ACIDS

[75] Inventors: Ibrahim S. Bechara, Boothwyn; Rocco L. Mascioli, Media; Philip J. Zaluska, Schnecksville, all of Pa.

[73] Assignee: Air Products and Chemicals, Inc., Allentown, Pa.

[21] Appl. No.: 954,131

[22] Filed: Oct. 23, 1978

Related U.S. Application Data

[62] Division of Ser. No. 746,313, Dec. 1, 1976, Pat. No. 4,134,994.

[51] Int. Cl.$^3$ .............. C07D 295/314; C07D 233/06; C07D 233/60
[52] U.S. Cl. .................. 544/119; 544/163; 544/351; 544/399; 546/205; 546/230; 548/341; 548/342
[58] Field of Search ............. 544/121, 163, 119, 399, 544/351; 546/205, 230; 548/341, 352

[56] References Cited

U.S. PATENT DOCUMENTS

| 3,557,184 | 1/1971 | Toepfl | 544/163 |
| 4,086,213 | 4/1978 | Bechara et al. | 528/48 |
| 4,134,994 | 1/1979 | Bechara et al. | 260/501.11 |

*Primary Examiner*—Henry R. Jiles
*Assistant Examiner*—R. W. Ramsuer
*Attorney, Agent, or Firm*—William F. Marsh; E. Eugene Innis

[57] ABSTRACT

Amine salts of tertiary amino acids have been found to be effective as catalysts for polyurethane synthesis and they have been found to exhibit delayed action, in many instances, in the polymerization of urethanes. Typically, the amine salts of tertiary amino acids are formed by initially reacting a primary or secondary amine with an aldehyde and disubstituted acid to form a Mannich adduct and then reacting the resulting Mannich acid adduct with an amine.

4 Claims, No Drawings

AMINE SALTS OF TERTIARY AMINO ACIDS

CROSS-REFERENCES TO RELATED APPLICATIONS

This application is a division of a copending application having U.S. Ser. No. 746,313, filed Dec. 1, 1976 now U.S. Pat. No. 4,134,994.

BACKGROUND OF THE INVENTION

1. Field

Polyurethanes, which are formed by reacting an isocyanate with a reactive hydrogen providing component, such as a polyol, have been widely used in preparing rigid and flexible foams, castings, adhesives and coatings. Typically, the reaction between the isocyanate and the polyol has been catalyzed by using various components such as amines, e.g. tertiary amines and organometallics, particularly organo tin compounds such as stannous octoate, dibutyl tin laurate, tin ethylhexanoate and so forth. The effectiveness of the catalyst is often measured by the cream time, which is the time required for the isocyanate and polyol syrup to turn from a clear solution to a creamy color; the gel time, which is the time required for polymer particles to form in the syrup; rise time, which is the time required for the syrup to rise to its maximum height; and cure time which is the time to reach a track-free state.

In some applications for polyurethanes it is desirable to effect reaction in the shortest time possible and, therefore, catalysts having tremendous activity are desired. In some applications, though, as in the molding of intricate parts or large objects, it may be desirable to keep the polyurethane composition in a fluid state for an extended time to permit the composition to completely fill the mold or flow into the cracks and crevices of the mold. Then, once the mold is completely filled, it is desirable to effect polymerization of the polyurethane in the shortest time possible so that the finished parts can be removed and the mold recharged with new materials. In this regard, it is desirable to delay the intial reaction, but after reaction commences then catalyze the polymerization rate. To do this it is necessary to extend the cream time to permit the polyurethane composition to penetrate the cracks and crevices in the mold and to extend the gelation time as the polyurethane foam on gelling becomes intractable and resists molding. However, once the reaction beings, it is desirable to end up with a rise and cure time comparable to those achieved by active catalysts as this will permit greater productivity.

2. Description of the Prior Art

Organometallics and particularly organo tin compounds such as tin ethylhexanoate, tin isooctoate, tin napthenate, di-n-butyl tin dilaurate; dibutyl tin diacetate, and tertiary nitrogen tin compounds such as dibutyl-tin-di(pyridine-4-carboxylic acid esters) as shown in U.S. Pat. No. 3,595,734; and U.S. Pat. No. 3,164,557 have been used to catalyze urethane reactions.

Amine compounds and particularly tertiary amines or their salts have been used as catalysts for polyurethanes. Examples of amines which are suited for catalyzing polyurethane reactions are dimethyl benzylamine, triethylenediamine, trimethylamine; alkanolamines such as diethanolamine, triethanolamine, N-diethyl-ethanolamine; N-hydroxyalkyl substituted imidazoles and N-vinyl pyrrolidone as shown in U.S. Pat. Nos. 3,645,927; 3,450,648; 3,448,065 and 3,746,663.

U.S. Pat. Nos. 3,620,986 and 3,580,868 show that Mannich bases of secondary amines and phenols can be used for catalyzing an isocyanate-hydroxyl reaction. Generally, some aminoalcohol is present and the phenol radical may contain an active hydrogen atom, e.g. COOH, CONH$_2$, OH, etc., which can condense into the urethane structure. Typically, these Mannich bases are formed by reacting dimethylamine, formaldehyde, aminoalcohol and a phenol, e.g. Bisphenol A, or salicylic acid amide.

Although the above references indicate the compositions have catalytic activity, a number of references have suggested similar but different compositions as being useful as delayed action catalysts (DAC), i.e. those which initially delay and then catalyze the isocyanate-hydroxyl reaction. For example, chelating agents, e.g. beta-diketones and beta carbonyls with aminefree organometallics have been used. Examples of beta-diketones useful as a delayed action catalyst in polyurethane chemistry include 2,4-hexanedione, acetylacetone, 1,cyclohexyl-1, 3 butanedione; beta-hydroxy ketones, e.g. beta hydroxy quinoline, 1-hydroxy-9-fluorenone, and alpha-hydroxy ketones, e.g. benzoin, acetoin and others as shown in U.S. Pat. No. 3,635,906.

Another example of a delayed action catalyst for the preparation of foamed polyurethane resins is shown in U.S. Pat. No. 2,932,621. This patent discloses that amine salts of dicarboxylic acids notably the hydroxy tertiary amine salts of oxalic acid are particularly effective in delaying the intial reaction between an isocyanate and hydroxyl group, but after an appropriate lapse of time, they become fully effective and cause the reaction to proceed to completion smoothly, rapidly and efficiently.

It has been proposed to use quarternary ammonium salts of Mannich bases as a delayed action catalyst for the reaction between an isocyanate and polyol to form polyurethanes. Initially, the quarternary ammonium salt has little catalytic effect, but during the reaction it decomposes to form tertiary amine which can assist in catalyzing the reaction. Examples of quarternary ammonium salts of Mannich bases are shown in U.S. Pat. No. 2,950,262 and are prepared by reacting a secondary amine with an aldehyde and a ketone such as cyclohexanone and then reacting the Mannich base with an organic halide to form the quarternary ammonium salt.

SUMMARY OF THE INVENTION

This invention relates to amine salts of tertiary amino acids. These amine salts are represented by the formula

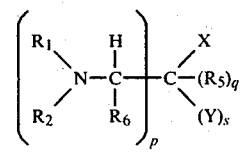

wherein in the formula:
R$_1$ and R$_2$ are combined to form a cyclic amine selected from the group consisting of a piperidinyl, piperizinyl, morpholino, imidazolo and imidazolino radicals;

R₅ is hydrogen, a lower aklyl group having from 1 to 6 carbon atoms, an alkenyl group having from 2 to 6 carbon atoms, an aryl group, a cycloaliphatic or alkyl substituted cycloaliphatic group with the alkyl portion having from 1 to 6 carbons, or a keto alkyl group with the alkyl portion having from 1 to 6 carbon atoms;

R₆ is hydrogen, or a radical selected from the group consisting of alkyl, phenyl and napthyl groups;

X is an amine salt of a carboxylic acid group;

Y is a nitrile group; and q is 0 or 1; p is 1 or 2; s is 0 or 1; and p+q+s is 3.

Advantages of the amine of tertiary amino acid catalysts of this invention include:

the ability to delay, as compared to conventional amine catalysts, the initial reaction between an isocyanate and an active hydrogen containing compound in the formation of a polyurethane;

the ability to catalyze the reaction between an isocyanate and an active hydrogen containing compound;

the ability to form an organometallic catalyzed polyurethane molding composition having excellent flow during initial stages by extending the cream and gelation time and yet end up with a desirable rise and cure time which often is close to those obtained with conventional catalyst compositions; and the ability, by virtue of being thermally sensitive, to generate additional reactive amine for catalyzing and enhancing the cure rate.

DESCRIPTION OF THE PREFERRED EMBODIMENTS

Broadly, the amine salts of the tertiary amino acids of this invention can be visualized as amine salts of Mannich type tertiary amino acid adducts having at least monofunctionality in terms of tertiary amine, and at least monofunctionality and preferably at least difunctionality in the form of an amine salt.

The Mannich type tertiary amino acid adducts typically are formed by reacting a primary and preferably a secondary amine with an aldehyde having sufficient capability to react with the amine hydrogen and form a terminal methylol group and an organic compound having a hydrogen atom sufficiently reactive to undergo the Mannich addition, and having pendent acid functionality or functionality which can be converted to the acid form and then reacting the thus formed Mannich tertiary amino acid adduct with an amine to form the salt. Further description of the preparation of the Mannich adduct and type can be found in copending application having U.S. Ser. No. 717,579, and a filing date of Aug. 26, 1976, now U.S. Pat. No. 4,086,213, and is incorporated by reference.

In preparing the Mannich type adducts described, suitable amines generally are lower alkyl amines having from 1 to 15 carbon atoms, and preferably 1 to 3 carbon atoms, lower alkanol amines where the alkanol portion has from 2 to 4 carbon atoms; phenyl amines such as mono and dibenzylamine, cyclic amines such as cyclohexylamine and dicyclohexylamine; piperidine; piperizine; imidazole, aralkylene amines, e.g. ethylbenzylamines; heterocyclic amines, e.g. morpholine. The amines can be substituted with various functional groups, e.g. alkyl, alkoxy, ether and hydroxyl so long as the functionality does not interfere with the reaction or impart an adverse characteristic to the resulting polyurethane resin. The preferred substituted group is a hydroxyl group as it does not interfere with the reaction and tends to aid the delay in the initial urethane reaction and thereby lengthen the cream time. Those amines best suited for forming the Mannich type are morpholine, diethanolamine, ethanolamine, piperidine and piperizine.

The second component used in forming the Mannich adduct is an aldehyde. Aldehydes and substituted aldehydes useful in forming the Mannich adducts are well known and can be used here. As taught in the art, these aldehydes must have a pendant aldehyde group which is sufficiently reactive to form the Mannich adduct. Typically, these aldehydes are activated, as for example, by an unsaturated group in conjugated relationship with the carbonyl aldehyde. Examples of aldehydes best suited for practicing the invention are formaldehyde, benzaldehyde, furfuraldehyde, napthaldehyde, and substituted aldehydes such as nitrobenzaldehyde, nitrofurfural, cyanofurfuraldehyde and the like. For reasons of efficiency and economy, formaldehyde is the preferred aldehyde used in forming the adduct.

The remaining component necessary for forming the Mannich adduct is an organic compound having at least one hydrogen atom sufficiently reactive for undergoing a Mannich reaction. Generally in such compounds, the hydrogen atom is positioned in a methylene group alpha positioned to a carbonyl group such as a ketone, a carboxylic acid ester or an acid group. Further, the organic compound should have a pendant carboxylic acid or nitrile group or a structure, e.g. ketone or ester which permits the formation of a carboxylic acid. The acid then can be neutralized with amine and converted to the salt. Examples of organic compounds having at least one active hydrogen atom, and in some instances, two active hydrogen atoms suited for practicing the invention include disubstituted saturated acids such as malonic acid, benzyl malonic acid, lower alkyl ($C_1$–$C_3$) malonic acids, furfuryl malonic acid, alkenyl malonic acids, e.g. allyl malonic acid; cyanoacetic acid and keto acids, e.g. 2 ketobutyric acid.

The amine salts of the invention can be formed by reacting the amino acids with amines such as ethanolamine, diethanolamine, triethanolamine, tri-n-propanolamine, methylamine, ethylamine, propylamine, benzylamine, triethylamine, cyclohexylamine, etc. Highly reactive tertiary amines such as bis(dimethylaminoethyl) ether and triethylenediamine can also be used to form the amine salts and these catalysts are particularly effective for enhancing the rate of the urethane reaction. Generally, the less active amines, such as ethanol and diethanol amine result in producing a less active catalyst. Because the tertiary amine is tied to the Mannich adduct, though, the cream time is lengthened substantially over that which is obtained by using tertiary amine alone.

Examples of amine salts of Mannich type adducts include: bis-tri-n-propanolamine salt of bis(hydroxyethylamino) methyl malonic acid, diethanolamine salt of hydroxyethylamino methyl malonic acid, monomethylamine salt of bis(hydroxyethylamino) furfuryl malonic acid, bis-triethylenediamine salt of bis(hydroxyethylamino) benzyl malonic acid, bis-triethylenediamine salt of morpholino benzyl malonic acid, bis-dimethylamine salt of morpholine methyl malonic acid, methylamine salt of bis(piperidinylmethyl) acetic acid, bis-tri-n-propanolamine salt of diglycolamino methyl malonic acid, propanolamine salt of bis(piperidinylmethyl) acetic acid, triethanolamine salt of bis(imidazolo methyl) acetic acid, bis-trimethylamine salt of piperidinyl methyl malonic acid and triethylenediamine salt of morpholino benzyl cyanoacetic acid.

The amine salts of the tertiary amino acids of this invention can be utilized with other conventional polyurethane catalysts without detracting from the overall benefits. A conventional catalyst that is quite acceptable as a cocatalyst is an organometallic, suitably an organo tin composition such as dibutyl tin dilaurate, dibutyl tin diacetate, diethyl tin diacetate, dihexyl tin diacetate, stannous octoate, stannous decanoate and dioctyl tin oxide.

Representative polyisocyanates suited for producing polyurethanes in practicing this invention are the aliphatic and aromatic polyvalent isocyanates. Examples of aliphatic isocyanates include alkylene diisocyanates such as tri, tetra and hexamethylene diisocyanates; arylene diisocyanates and their alkylation products such as phenylene diisocyanate, naphthylene diisocyanate, diphenylmethane diisocyanate, toluene diisocyanate, di and triisopropyl benzene diisocyanate and triphenylmethane triisocyanates; triesters of isocyanato-phenyltriphosphoric acid; triesters of para-isocyanato phenyl phosphoric acid; aralkyl diisocyanates such as 1-(isocyanato phenol-ethyl) isocyanate or xylene diisocyanate.

Suitable reactive Zerewitinoff compounds, e.g., polyols for forming the polyurethanes include aliphatic polyether polyols prepared from the reaction of ethylene or propylene oxides or mixtures thereof with a glycol; glycols such as ethylene glycol, propylene glycol, butylene glycol, tetramethylene glycol, hexamethylene glycol, and triols such as glycerol, trimethylolpropane, trimethylol ethane, and higher polyols such as pentaerythritol, sorbitol, caster oil, polyvinyl alcohol, sucrose, dextrose, methyl glycoside and the like; amino polyols made by the condensation of alkylene oxides and alkanol amines such as tetrahydroxyethylenediamine, tetrahydroxypropyl ethylenediamine; other organic compounds having an active hydrogen atom are amines such as triethanolamine, methylamine, diethanolamine, phenylenediamine, tolylenediamine, piperizine and the like.

The polyols also can be incorporated into a polymer and reacted with the isocyanates as in the case of polyesters. A polyester, as is known, is prepared by the reaction between a dicarboxylic acid and a polyol, e.g. a glycol. Examples of conventional dicarboxylic acids suited for manufacturing polyester polyols include succinic, glutaric, adipic, sebacic, phthallic, terephthallic, maleic, fumaric, itaconic, citraconic, and the like. Glycols include, ethylene glycol, propylene glycol and butylene glycol.

In the preparation of polyurethanes, conventional additives can be utilized for their desired effect without departing or detracting from the advantageous aspects of the catalysts of this invention. For example, blowing agents such as water or a volatile organic such as dichlorodifluoromethane, dichlorofluoromethane, trichloromonofluoromethane, dichlorofluoromethane, difluorodichoroethane, methylene chloride, carbontetrachloride, butane, pentane, and the like.

Foam stabilizers or surfactants are other additives which can be added for enhancing the retention of gas generated during the polymerization reaction and such stabilizers include silicone block polymers comprising polyalkylene glycol units, n-vinyl pyrrolidone, or n-vinyl pyrrolidone-dibutyl maleic copolymers or n-vinyl pyrrolidone-dibutyl maleate (vinyl acetate). Other examples are shown in U.S. Pat. No. 3,746,663.

In preparing the polyurethanes, the amine salt of a Mannich acid adduct is added to the urethane composition in at least a sufficient or effective proportion for enhancing the cure rate of the urethane. When the catalyst is used alone, generally from about 0.1 to about 5 parts by weight per 100 parts and preferably about 0.5 to about 1.5 per 100 parts by weight of reactive Zerewitinoff hydrogen compound, e.g. polyol are included. When less than about 0.1 parts are added to the composition, the catalyst is not present in sufficient proportion to substantially influence the cure rate of the polyurethane. When more than about 3.5 parts catalyst are added to the urethane composition, too much amine may be introduced and amine odor may be observed. For reasons of economy, the catalyst concentration is preferably from about 0.5 to about 1.5 parts.

Often where the organo portion of the amine salt of tertiary amino acid is relatively small or negated by the fact that a hydroxyl or other polar group is present, it may be necessary to use a solvent to disperse the catalyst in the urethane syrup. Virtually any solvent may be used which does not compete with the isocyanate-active hydrogen to form a polyurethane, or does not adversely affect the resultant polyurethane. Conventional solvents such as glycols, e.g. propylene glycol, ethylene glycol, dipropylene glycol, ethylene carbonate, and amino-nitrile compositions such as cyanoethyl-diethanolamine, which is also a catalyst, can be used as a solvent.

Organometallic catalysts may be included in polyurethane manufacture along with the amine salts in a proportion of from about 0.005 to about 0.5, and preferably 0.01 to 0.2 parts by weight per 100 parts of active Zerewitinoff hydrogen compound. Variations within this broad range are practiced depending on whether, for example, high and low density polyurethanes are prepared and seems to be no significant enhancement of catalytic activity or of other desired features to warrant the additional expenditure and usage of the catalyst.

The following examples are provided to illustrate preferred embodiments in the invention and are not intended to restrict the scope thereof. All parts are parts by weight, all percentages are expressed as weight percentages, and all temperatures are in °C. unless otherwise specified.

EXAMPLE 1

Bis-(hydroxyethyl)amino benzyl malonic acid was prepared conventionally in a flask equipped with a stirrer and reflux condenser by first charging 0.1 mol of malonic acid, 0.1 mol of diethanol amine and 100 cc methanol. The contents were warmed to a temperature of about 20° C. and then 0.1 benzaldehyde were added to the flask and the reaction commenced. After refluxing the reaction mixture for 1 hour, the methanol was removed from the reaction mixture by coupling the flask to a vacuum source and heating to a temperature of about 50° C. The residue remaining in the flask then was triturated in acetone and the resulting acid isolated by filtration.

The bis-triethylenediamine salt of the acid was prepared by mixing 0.1 m of the methanolic solution of the acid with 0.2 m triethylene diamine at room temperature (25° C.) for 30 minutes, after which the methanol was removed under reduced pressure.

EXAMPLE 2

Morpholino benzyl cyanoacetic acid was prepared in the same manner as the acid of Example 1 except that morpholine was substituted for diethanolamine and cyanoacetic acid for malonic acid. The monotriethylenediamine salt of the cyanoacetic acid adduct was prepared in the same manner as the amine salt of Example 1.

EXAMPLE 3

Approximately 100 cc of water and 0.2 mols (21.1 grams) of malonic acid and 0.4 mols (27.4 grams) of imidazole were charged to a round bottom flask. Then 0.4 mols formaldehyde as a 35% aqueous solution were added over a period of time to the mixture of water, malonic acid and imidazole. The resulting mixture was stirred for about 36 hours at 25° C. after which the contents were heated to a temperature of 50° C. and the water removed by vacuum. The resulting product was bis-(imidazole methyl) acetic acid.

EXAMPLE 4

Approximately 100 cc of methanol, 0.1 mols of malonic acid, 0.1 mols of diethanolamine, and 0.1 mols of furfuraldehyde were charged to a round bottom flask. The contents were refluxed for two hours, and then the methanol removed by evacuation. The product obtained was bis-(hydroxyethyl) furfuryl malonic acid.

The triethylenediamine salt of the above product is prepared in the same procedure as the composition in Example 1.

EXAMPLE 5

Conventional high density rigid polyurethane foams were prepared from the basic formulation below in conventional manner. In preparing these polyurethane foams, the catalyst, comprising an amine salt of a Mannich adduct (as indicated), and organometallic (as indicated) and the concentration of each catalyst component were varied to determine the overall effect on the foam formulation. The polyurethane foams were evaluated for cream time, gelation time, and cure time.

The components used for preparing the high density foam were as follows:

| Component | Amount, parts by weight |
|---|---|
| Mondur ® MR Isocyanate | 100 |
| NIAX ® DAS-361 Polyol | 65 |
| Thanol ® G-400 Polyol | 27.7 |
| Polylite ® 34-400 Polyol | 5.0 |
| Water | 0.6 |
| DC-193 | 0.8 |
| Tertiary amino acid or nitrile catalyst parts/100 parts polyol (php) | 0.5–1.5 |
| Organometallic catalyst parts/100 parts polyol (php) | 0.005–0.5 |

(1) Mondur MR Isocyanate is crude 4,4'methylene bisphenylisocyanate having an isocyanate equivalent of about 133, a functionality of about 2.7–2.9 and a viscosity of about 150–250 cps.

(2) NIAX DAX-361 Polyol is a sucrose/amine polyol having a hydroxyl number of 360.

(3) Thanol G-400 Polyol is a glycerol polyol having a hydroxyl number of 400.

(4) Polylite 34-400 Polyol is an amino polyol having a hydroxyl number of 790.

(5) In the examples to follow where a previous example is given, as the catalyst used but a different amine indicated as a solvent, that amine was used in place of the particular amine in the previous example; TEDA refers to triethylenediamine; DEA refers to diethanolamine; DPG refers to dipropylene glycol; PG refers to propylene glycol; T-12 refers to dibutyl tin dilaurate, php refers to the parts of catalyst (including solvent if used) per 100 parts polyol.

The results of the formulation testing is set forth in Table 1.

TABLE
HIGH DENSITY RIGID FOAM

| Catalyst php | Solvent | Organometallic php | Cream Time Sec. | Gel Time Sec. | Tack Free Cure Time Sec. |
|---|---|---|---|---|---|
| Ex. 1 (0.5) | (neat) | — | 61 | 132 | 176 |
| Ex. 1 (0.7) | (neat) | — | 53 | 113 | 160 |
| Ex. 1 (1.0) | (neat) | — | 44 | 93 | 125 |
| Ex. 1 (0.5) | (neat) | T-12 (0.03) | 48 | 77 | 86 |
| Ex. 1 (1.0) | (neat) | T-12 (0.04) | 43 | 69 | 79 |
| Ex. 1 (0.5) | (neat) | T-12 (0.04) | 46 | 71 | 78 |
| Ex. 1 (1.0) | (neat) | T-12 (0.04) | 40 | 64 | 72 |
| Ex. 1 (0.5) | (neat) | T-12 (0.05) | 44 | 63 | 69 |
| Ex. 1 (1.0) | (neat) | T-12 (0.05) | 37 | 61 | 65 |
| Ex. 2 (0.5) | (50% DPG) | — | 75 | 157 | 227 |
| Ex. 2 (1.5) | (50% DPG) | — | 50 | 107 | 154 |
| Ex. 2 (0.5) | (50% DPG) | T-12 (0.01) | 53 | 100 | 125 |
| Ex. 2 (1.5) | (50% DPG) | T-12 (0.01) | 43 | 82 | 105 |
| Ex. 2 (1.5) | (50% DPG) | T-12 (0.03) | 33 | 90 | 111 |
| ethylene diamine (0.4) | | | 60 | 197 | 6 min. |
| diethanolamine (0.4) | | | 68 | 244 | 6 min. |
| diethylenetriamine (0.4) | | | 59 | 228 | 6 min. |
| n-butylamine | | | 61 | 244 | 6 min. |
| TEDA (0.23) | 67% DPG | — | 34 | 81 | 106 |
| — | — | T-12 (0.03) | 46 | 82 | 94 |
| — | — | T-12 (0.04) | 44 | 78 | 87 |
| — | — | T-12 (0.05) | 33 | 61 | 68 |

EXAMPLE 6

Conventional low density rigid polyurethane foam formulations utilizing the components set forth below were prepared in conventional manner. In these polyurethane foams, the catalysts comprising an amino acid and organometallic and the concentration were varied. The basic formulation used for the low density rigid polyurethane foam was as follows:

| Component | Amount, parts |
|---|---|
| Hylene® TIC[1] | 105 |
| RS-6406 Polyol[2] | 109 |
| DC193[3] Surfactant | 1.5 |
| R11[4] Blowing Agent | 47 |

(1) Hylene TIC is an undistilled, technical grade of tolylene diisocyanate typically having an isocyanate content of 38.75 to 39.75%, an amine equivalent of 105.5 to 108 and a viscosity at 25° C. of 15 to 75 cps.

(2) RS-6406 Polyol is a sucrose/amine polyol having a hydroxyl number 475.

(3) DC-193 Surfactants are polysiloxane polyoxyalkylene block copolymers. Examples are shown in U.S. Pat. Nos. 2,834,748 and 2,917,480.

(4) R-11 Blowing Agent is trichloromonofluoromethane.

(5) See the exerpt for high density formulations for an explanation of terms used on page 20, paragraph (5). The results are shown in Table 2.

TABLE 2

LOW DENSITY RIGID FOAM

| Catalyst php | Solvent | Organometallic php | Cream Time Sec. | Gel Time Sec. | Tack Free Cure Time Sec. | Shrinkage | Friability |
|---|---|---|---|---|---|---|---|
| dimethylcyclohexylamine (0.8) | — | | 18 | 77 | 168 | none | none |
| TEDA (0.17) | 67% DPG | — | 30 | 106 | 164 | slight | moderate |
| TEDA (0.43) | 67% DPG | — | 11 | 50 | 75 | none | none |
| — | | T-12 (0.2) | 38 | 70 | 98 | moderate | moderate |
| bis-DEA salt of malonic acid (0.05) | | T-12 (0.08) | 39 | 117 | 230 | slight-moderate | very slight |
| bis-DEA salt of malonic acid (1.0) | | T-12 (0.08) | 36 | 123 | 237 | moderate | slight |
| bis-DEA salt of malonic acid (0.5) | | T-12 (0.1) | 37 | 115 | 241 | moderate | slight |
| bis-DEA salt of malonic acid (1.0) | | T-12 (0.1) | 34 | 117 | 245 | moderate-severe | slight |
| mono DEA salt of malonic acid (0.5) | | T-12 (0.08) | 36 | 114 | 221 | slight-moderate | very slight |
| mono DEA salt of malonic acid (1.0) | | T-12 (0.08) | 34 | 133 | 259 | severe | slight |
| mono DEA salt of malonic acid (0.5) | | T-12 (0.1) | 36 | 103 | 187 | slight-moderate | slight |
| mono DEA salt of malonic acid (1.0) | | T-12 (0.1) | 33 | 111 | 208 | slight | slight |

EXAMPLE 7

Conventional microcellular polyurethane foam formulations were prepared in the usual manner by mixing
87 parts of CP-4701 polyol,
13 parts of 1,4-butanediol,
1.00 parts of L-5303 Silicone Surfactant and
0.30 parts of water to form a polyol premix.
Then the tertiary amino acid (DAC) and organometallic catalyst were added and the type and concentration of each was varied as indicated.

After the catalysts were blended with the premix, 50 parts Mondur MR isocyanate were added to the premix and the resulting syrup poured into a container and evaluated as indicated in Table 2. Terms used in the table correspond to Example 5, paragraph (5) for the high density formulations. In addition (1) CP-4701 Polyol—is a polyol made from glycerine and propylene and ethylene oxides and is marketed by the Dow Chemical Company, and (2) L-5303 Silicone—is a surfactant supplied by Union Carbide Corporation.

TABLE 3

MICROCELLULAR FOAM

| Catalyst php | Solvent | Organometallic php | Cream Time Sec. | Gel Time Sec. | Tack Free Cure Time Sec. |
|---|---|---|---|---|---|
| TEDA (0.2) | (66.6% DPG) | T-12 (0.03) | 27 | 36 | 49 |
| — | | T-12 (0.25) | 30 | 35 | 43 |
| Ex. 2 (1.0) | (50% DPG) | — | 272 | 400 | 600 |
| Ex. 2 (2.0) | (50% DPG) | — | 155 | 255 | 320 |
| Ex. 2 (0.5) | (50% DPG) | T-12 (0.04) | 81 | 100 | 125 |

TABLE 3-continued

| | | MICROCELLULAR FOAM | | | |
|---|---|---|---|---|---|
| Catalyst php | Solvent | Organometallic php | Cream Time Sec. | Gel Time Sec. | Tack Free Cure Time Sec. |
| Ex. 2 (1.0) | (50% DPG) | T-12 (0.04) | 72 | 90 | 110 |
| Ex. 2 (2.0) | (50% DPG) | T-12 (0.04) | 71 | 90 | 105 |
| — | — | T-12 (0.04) | 360+ | — | — |

We claim:

1. An amine salt of a tertiary amino acid represented by the formula:

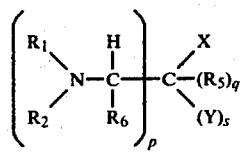

wherein in the formula:

$R_1$ and $R_2$ are combined to form a cyclic amine selected from the group consisting of piperidinyl, piperizinyl, morpholino, imidazolo and imidazolino radicals;

$R_5$ is hydrogen, a lower alkyl group having from 1 to 6 carbon atoms, an alkenyl group having from 2 to 6 carbon atoms, an aryl group, a cycloaliphatic or alkyl substituted cycloaliphatic group with the alkyl portion having from 1 to 6 carbons, or a keto alkyl group with the alkyl portion having from 1 to 6 carbon atoms;

$R_6$ is hydrogen, or a radical selected from the group consisting of alkyl, phenyl and napthyl groups;

X is an amine salt of a carboxylic acid group;

Y is a nitrile group; and p, q, and s are each 1.

2. The amine salt of claim 1 wherein $R_6$ is phenyl.

3. The amine salt of claim 1 wherein $R_5$ is hydrogen, methyl or benzyl.

4. The amine salt of claim 1 wherein X is a tertiary amine salt of carboxylic acid.

* * * * *

UNITED STATES PATENT AND TRADEMARK OFFICE
CERTIFICATE OF CORRECTION

PATENT NO. : 4,232,152
DATED : 4 November 1980
INVENTOR(S) : I.S. Bechara, R. L. Mascioli & P.J. Zaluska It is certified that error appears in the above-identified patent and that said Letters Patent are hereby corrected as shown below:

Column 2, Line 37
    After "has" and before "been", insert --also--

Column 6, Line 55
    After "0.1" and before "benzaldehyde", insert --mol--

Column 8, Line 43
    After "TABLE" insert --1--

Signed and Sealed this

Seventh Day of April 1981

[SEAL]

Attest:

RENE D. TEGTMEYER

*Attesting Officer*     *Acting Commissioner of Patents and Trademarks*